United States Patent
Reinbold et al.

(10) Patent No.: US 11,903,406 B2
(45) Date of Patent: Feb. 20, 2024

(54) METHOD FOR FERMENTING TOBACCO

(71) Applicant: American Snuff Company, LLC, Memphis, TN (US)

(72) Inventors: Robert S. Reinbold, Collierville, TN (US); John E. Bunch, Cary, NC (US)

(73) Assignee: American Snuff Company, LLC, Memphis, TN (US)

( * ) Notice: Subject to any disclaimer, the term of this patent is extended or adjusted under 35 U.S.C. 154(b) by 0 days.

(21) Appl. No.: 16/574,890

(22) Filed: Sep. 18, 2019

(65) Prior Publication Data

US 2021/0076730 A1     Mar. 18, 2021

(51) Int. Cl.
*A24B 15/20* (2006.01)
*C12N 1/20* (2006.01)
*C12R 1/44* (2006.01)
*C12R 1/225* (2006.01)

(52) U.S. Cl.
CPC .............. *A24B 15/20* (2013.01); *C12N 1/205* (2021.05); *C12R 2001/225* (2021.05); *C12R 2001/44* (2021.05)

(58) Field of Classification Search
CPC ................................ A24B 15/20; C12R 1/225
USPC ........................................................ 131/300
See application file for complete search history.

(56) References Cited

U.S. PATENT DOCUMENTS

| | | |
|---|---|---|
| 787,611 A | 4/1905 | Daniels, Jr. |
| 1,086,306 A | 2/1914 | Oelenheinz |
| 1,437,095 A | 11/1922 | Delling |
| 1,757,477 A | 5/1930 | Rosenhoch |
| 2,122,421 A | 7/1938 | Hawkinson |
| 2,148,147 A | 2/1939 | Baier |
| 2,170,107 A | 8/1939 | Baier |
| 2,274,649 A | 3/1942 | Baier |
| 2,770,239 A | 11/1956 | Prats et al. |
| 3,612,065 A | 10/1971 | Rosen |
| 3,851,653 A | 12/1974 | Rosen |
| 3,889,689 A | 6/1975 | Rosen |

(Continued)

FOREIGN PATENT DOCUMENTS

| | | |
|---|---|---|
| EP | 2529634 | 12/2012 |
| GB | 2542623 | 3/2017 |

(Continued)

OTHER PUBLICATIONS

How to Grow and Cure Tobacco at Home, dengarden, https://dengarden.com/gardening/Tobacco-Growing-and-Curing-at-Home (Year: 2019).*

(Continued)

*Primary Examiner* — Russell E Sparks
(74) *Attorney, Agent, or Firm* — Womble Bond Dickinson (US) LLP

(57) ABSTRACT

A method of preparing a tobacco material for use in a smokeless tobacco product is provided, the method including receiving a tobacco material, wherein the tobacco material has not been subjected to a fermentation process, blending the tobacco material with the final moist snuff product ingredients to form a tobacco composition having a moisture content of at least about 50%, packaging the tobacco composition in a final product packaging such that after a fermentation period of 7 to 28 days within the final product packaging the product is ready for direct sale and consumption.

16 Claims, 4 Drawing Sheets

(56) References Cited

U.S. PATENT DOCUMENTS

| | | | |
|---|---|---|---|
| 3,943,940 A | 3/1976 | Minami | |
| 3,943,945 A | 3/1976 | Rosen | |
| 4,143,666 A | 3/1979 | Rainer et al. | |
| 4,144,895 A | 3/1979 | Fiore | |
| 4,150,677 A | 4/1979 | Osborne, Jr. et al. | |
| 4,194,514 A | 3/1980 | Campbell | |
| 4,267,847 A | 5/1981 | Reid | |
| 4,289,147 A | 9/1981 | Wildman et al. | |
| 4,340,073 A | 7/1982 | de la Burde et al. | |
| 4,351,346 A | 9/1982 | Brummer et al. | |
| 4,359,059 A | 11/1982 | Brummer et al. | |
| 4,366,823 A | 1/1983 | Rainer et al. | |
| 4,366,824 A | 1/1983 | Rainer et al. | |
| 4,388,933 A | 6/1983 | Rainer et al. | |
| 4,506,682 A | 3/1985 | Muller | |
| 4,513,756 A * | 4/1985 | Pittman | A24B 13/00 131/111 |
| 4,528,993 A | 7/1985 | Sensabaugh, Jr. et al. | |
| 4,589,428 A | 5/1986 | Keritsis | |
| 4,605,016 A | 8/1986 | Soga et al. | |
| 4,641,667 A | 2/1987 | Schmekel et al. | |
| 4,660,577 A | 4/1987 | Sensabaugh et al. | |
| 4,716,911 A | 1/1988 | Poulose et al. | |
| 4,727,889 A | 3/1988 | Niven, Jr. et al. | |
| 4,848,373 A * | 7/1989 | Lenkey | A24B 15/20 131/309 |
| 4,887,618 A | 12/1989 | Bernasek et al. | |
| 4,941,484 A | 7/1990 | Clapp et al. | |
| 4,967,771 A | 11/1990 | Fagg et al. | |
| 4,986,286 A | 1/1991 | Roberts et al. | |
| 5,005,593 A | 4/1991 | Fagg | |
| 5,018,540 A | 5/1991 | Grubbs et al. | |
| 5,060,669 A | 10/1991 | White et al. | |
| 5,065,775 A | 11/1991 | Fagg | |
| 5,074,319 A | 12/1991 | White et al. | |
| 5,099,862 A | 3/1992 | White et al. | |
| 5,121,757 A | 6/1992 | White et al. | |
| 5,131,414 A | 7/1992 | Fagg et al. | |
| 5,131,415 A | 7/1992 | Munoz et al. | |
| 5,148,819 A | 9/1992 | Fagg | |
| 5,197,494 A | 3/1993 | Kramer | |
| 5,230,354 A | 7/1993 | Smith et al. | |
| 5,234,008 A | 8/1993 | Fagg | |
| 5,243,999 A | 9/1993 | Smith | |
| 5,259,403 A | 11/1993 | Guy et al. | |
| 5,301,694 A | 4/1994 | Raymond et al. | |
| 5,318,050 A | 6/1994 | Gonzalez-Parra et al. | |
| 5,343,879 A | 9/1994 | Teague | |
| 5,360,022 A | 11/1994 | Newton et al. | |
| 5,372,149 A | 12/1994 | Roth et al. | |
| 5,435,325 A | 7/1995 | Clapp et al. | |
| 5,445,169 A | 8/1995 | Brinkley et al. | |
| 5,713,376 A | 2/1998 | Berger | |
| 5,908,032 A | 6/1999 | Poindexter et al. | |
| 6,131,584 A | 10/2000 | Lauterbach | |
| 6,298,859 B1 | 10/2001 | Kierulff et al. | |
| 6,772,767 B2 | 8/2004 | Mua et al. | |
| 7,337,782 B2 | 3/2008 | Thompson | |
| 7,556,047 B2 | 7/2009 | Poindexter et al. | |
| 7,798,319 B1 * | 9/2010 | Bried | B65D 51/16 206/242 |
| 7,810,507 B2 * | 10/2010 | Dube | A24B 15/283 131/352 |
| 7,861,728 B2 | 1/2011 | Holton, Jr. et al. | |
| 8,440,023 B2 * | 5/2013 | Carroll | B65B 1/04 131/275 |
| 9,044,049 B2 * | 6/2015 | Winterson | B65B 9/207 |
| 9,271,524 B1 * | 3/2016 | Chipley | A24B 15/183 |
| 9,918,492 B2 * | 3/2018 | Marshall | A24B 15/28 |
| 10,472,642 B2 * | 11/2019 | Le Lay | A24B 15/245 |
| 2005/0178398 A1 | 8/2005 | Breslin et al. | |
| 2007/0062549 A1 | 3/2007 | Holton, Jr. et al. | |
| 2009/0025738 A1 | 1/2009 | Mua et al. | |
| 2011/0247640 A1 | 10/2011 | Beeson et al. | |
| 2011/0315035 A1 | 12/2011 | Mua et al. | |
| 2012/0067361 A1 | 3/2012 | Bjoerkholm et al. | |
| 2013/0276801 A1 | 10/2013 | Byrd, Jr. et al. | |
| 2017/0020183 A1 | 1/2017 | Bjoerkholm | |
| 2017/0112183 A1 | 4/2017 | Bjoerkholm | |
| 2017/0280764 A1 | 10/2017 | Sahlen et al. | |
| 2020/0196658 A1 | 6/2020 | McClanahan et al. | |

FOREIGN PATENT DOCUMENTS

| | | |
|---|---|---|
| WO | WO 96/31255 | 10/1996 |
| WO | WO 2005/063060 | 7/2005 |
| WO | WO 2015/003883 | 1/2015 |
| WO | WO 2015/063485 | 5/2015 |

OTHER PUBLICATIONS

Janus Airferm Sample Anaerobic Yeast Fermentation, Fisher, P. R., Newton, R. P., Brown & Williamson Tobacco Corp., Research & Development Department, Truth Tobacco Industry Documents, https://www.industrydocuments.ucsf.edu/tobacco/docs/#id=sxlj0211 (Year: 2006).*

Snuff and its Manufacture, Scientific American, Springer Nature America, Inc., https://www.scientificamerican.com/article/snuff-and-its-manufacture/ (Year: 1852).*

Merriam-Webster Dictionary, Definition of Individual, https://www.merriam-webster.com/dictionary/individual (Year: 2022).*

What is a Bulk Module Pack, O.Berk, User Joel, https://www.oberk.com/packaging-crash-course/qqm-bulk-module-pallet (Year: 2015).*

Proud Water: Small Mackay bottled water company offers taste of Idaho, local jobs, Painter, J., Post Register, https://www.postregister.com/news/local/proud-water-small-mackay-bottled-water-company-o erstasteof-idaho-local-jobs/article_fd01b0db-de9a-59d0-8316-2ba173c608d2.html (Year: 2019).*

* cited by examiner

US 11,903,406 B2

METHOD FOR FERMENTING TOBACCO

FIELD OF THE INVENTION

The present disclosure relates to products made or derived from tobacco, or that otherwise incorporate tobacco, and are intended for human consumption.

BACKGROUND

Cigarettes, cigars and pipes are popular smoking articles that employ tobacco in various forms. Such smoking articles are used by heating or burning tobacco, and aerosol (e.g., smoke) is inhaled by the smoker. Tobacco also may be enjoyed in a so-called "smokeless" form. Particularly popular smokeless tobacco products are employed by inserting some form of processed tobacco or tobacco-containing formulation into the mouth of the user.

Various types of smokeless tobacco products are known. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; 2009/0293889 to Kumar et al.; 2010/0291245 to Gao et al; and 2011/0139164 to Mua et al.; PCT WO 04/095959 to Arnarp et al. and WO 2010/132444 to Atchley; each of which is incorporated herein by reference.

One type of smokeless tobacco product is referred to as "moist oral snuff", or in some countries "snus." In Europe, representative types of moist snuff products, commonly referred to as "snus," are manufactured throughout Europe, particularly in Sweden, by or through companies such as Swedish Match AB, Fiedler & Lundgren AB, Gustavus AB, Skandinavisk Tobakskompagni A/S, and Rocker Production AB. Moist oral snuff products and other related smokeless tobacco products available in the U.S.A. are marketed under the tradenames CAMEL Snus®, CAMEL Orbs®, CAMEL Strips® and CAMEL Sticks® by R. J. Reynolds Tobacco Company; GRIZZLY® moist tobacco, KODIAK® moist tobacco, LEVI GARRETT® loose tobacco and TAYLOR'S PRIDE® loose tobacco by American Snuff Company, LLC; KAYAK® moist snuff and CHATTANOOGA CHEW® chewing tobacco by Swisher International, Inc.; REDMAN® chewing tobacco by Pinkerton Tobacco Co. LP; COPENHAGEN® moist tobacco, COPENHAGEN® Pouches, SKOAL® Bandits, SKOAL® Pouches, RED SEAL® long cut and REVEL® Mint Tobacco Packs by U.S. Smokeless Tobacco Company; and MARLBORO® Snus and Taboka by Philip Morris USA. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard.

Through the years, various treatment methods and additives have been proposed for altering the overall character or nature of tobacco materials utilized in tobacco compositions. For example, additives or treatment processes are sometimes utilized in order to alter the chemistry or sensory properties of the tobacco material, or in the case of smokable tobacco materials, to alter the chemistry or sensory properties of mainstream smoke generated by smoking articles including the tobacco material. In some cases, a fermentation process can be used to impart desired sensory properties to the tobacco material, or a desired physical nature or texture to the tobacco material.

It would be desirable in the art to provide further methods for altering the character and nature of tobacco (and tobacco compositions and formulations) useful in smoking articles or smokeless tobacco products. In particular, it would be desirable to provide cost effective and efficient fermentation processes.

BRIEF SUMMARY

The present disclosure provides a method of processing a tobacco material. As described in more detail below, processes of the present disclosure can include the step of fermenting a tobacco material in the final product packaging until it is ready for direct sale and consumption.

Various conventional processes for providing a moist oral snuff composition include (i) aging a tobacco material for about three years in a large container so the tobacco can go through some biochemical changes to help flavor and texture; (ii) blending different types of whole leaf aged tobacco and adding water to reach a moisture content of about 35%; (iii) fermenting the blend in barrels (750 pounds) for up to 8 weeks, during which time the barrels are turned 2 to 4 times to redistribute the tobacco to aid the fermentation (this step is often referred to as a primary fermentation step); (iv) when the primary fermentation is complete, based on desirable chemical parameters, chopping and drying the blended tobacco which thereby ends the primary fermentation; (v) adding casing materials, water and any other final product ingredients to the dried and chopped tobacco blend to form a tobacco composition; (vi) placing the tobacco composition into final product containers (e.g., pucks, cans, etc.) and putting the final product containers into sleeves which are then put into boxes and placed on palettes; and (vii) allowing the tobacco in the final product containers to undergo a secondary fermentation inside the container wherein the organic acid profile changes (typically around 18 days), and then putting the final product containers into the consumer distribution system. Generally, the final product containers have a self-life of about 6 months.

According to embodiments of the present disclosure, a method for providing a moist oral snuff composition includes (i) aging a tobacco material for about three years in a large container so the tobacco can go through some biochemical changes to help flavor and texture; (ii) blending different types of whole leaf aged tobacco (iii) chopping the aged tobacco material; (iv) adding casing materials, water and any other final product ingredients to the chopped tobacco blend to form a tobacco composition; (v) placing the tobacco composition into final product containers (e.g., pucks, cans, etc.) and putting the final product containers into sleeves which are then put into boxes and placed on palettes; and (vi) allowing the tobacco in the final product containers to undergo a primary fermentation inside the container wherein the organic acid profile changes (typically around 25 days or longer), and then putting the final product containers into the consumer distribution system.

A method of preparing a smokeless tobacco product is provided herein. The method includes: (i) receiving an aged tobacco material, wherein the aged tobacco material has not been subjected to a fermentation process; (ii) adding water and casing components to the aged tobacco material to form a tobacco composition having a moisture content of at least about 40%; (iii) blending all components of the finished product; (iv) packaging the tobacco composition in a storage container useful for storing the tobacco composition (e.g., final consumer distribution package/container); and (v) allowing the tobacco composition to ferment in the container for at least 25 days. It is noted that the step of packaging the tobacco compositions can include securing and/or sealing the container such that the final product container is ready to be offered for sale to consumers. The storage container can be an individual product container configured for consumer product distribution. In various embodiments, the tobacco material is not subjected to any substantial fermentation process prior to the fermentation in the container. In various embodiments of the methods described herein, smokeless tobacco product is moist oral snuff.

In some embodiments, the moisture content of the tobacco composition is about 40-60%, or about 51-53% prior to the step of packaging the tobacco composition such that upon packaging, the composition within the container has such a moisture content.

In various embodiments, the method further includes adding at least one additive (e.g., one or more casing materials) to the tobacco material prior to packaging the tobacco composition. The additive can be selected from the group consisting of water, flavorants, binders, colorants, pH adjusters, buffering agents, fillers, disintegration aids, humectants, antioxidants, oral care ingredients, preservatives, additives derived from herbal or botanical sources, and mixtures thereof. In certain embodiments, the additive includes at least one salt. To obtain the desired moisture content within the range noted above, it can be necessary to consider the effect of all such additives to be included prior to packaging as the moisture content of the tobacco composition can be affected by any additional ingredients added to the tobacco material.

A method of preparing a smokeless tobacco product is provided herein, the method comprising: (i) adding water to the tobacco material that has not been subjected to a substantial fermentation process to form a tobacco composition; (ii) packaging the tobacco composition in a container intended as a salable container for retail distribution of the smokeless tobacco product; and (iii) allowing the tobacco composition to ferment in the container for a period of time such that the tobacco composition is ready for consumer use. It is noted that in various embodiments, packaging the tobacco composition in the container can be done relatively quickly (e.g., 5 hours or less, two hours or less, or one hour or less) such that the tobacco composition retains the desired moisture levels. The method can further include sealing or at least partially sealing the container with a label or wrapper of a pervious or impervious material, wherein the label is configured to substantially cover at least a portion of the outer surface of the container.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

DETAILED DESCRIPTION

Figure 1:
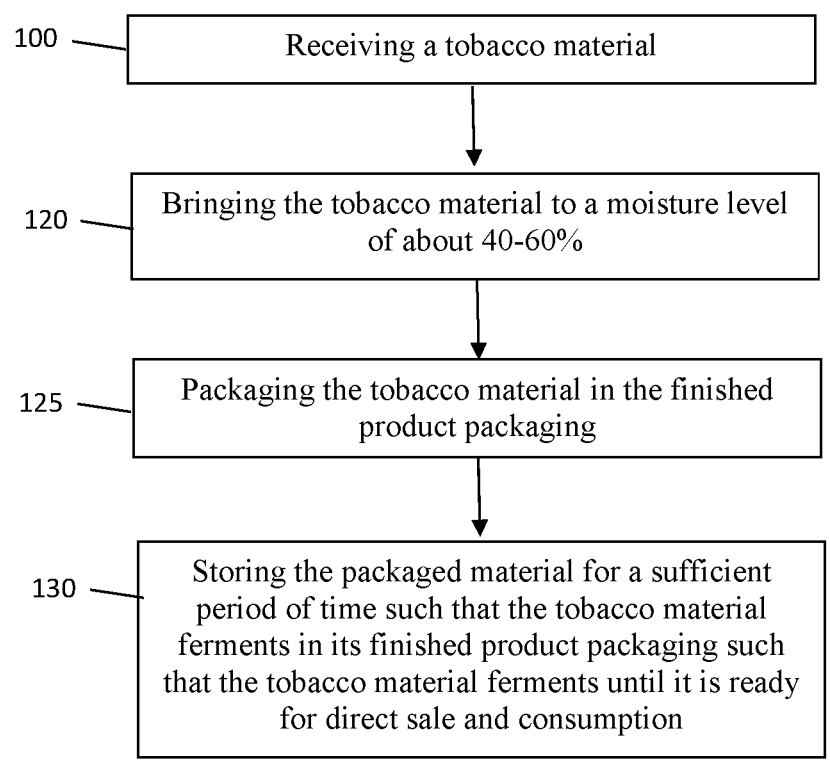
FIG. 1 is a flow chart illustrating the general steps for preparing a moist snuff tobacco product according to an embodiment of the present disclosure.

Aspects of the present disclosure now will be described more fully hereinafter. This invention may, however, be embodied in many different forms and should not be construed as limited to the embodiments set forth herein; rather, these embodiments are provided so that this disclosure will be thorough and complete, and will fully convey the scope of the present disclosure to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present disclosure provides, in particular, methods for fermenting tobacco and tobacco-containing materials, and to the materials produced from such processes. A fermentation process is generally characterized by transformation of the tobacco material by one or more microorganisms, which can be associated with the tobacco material itself and/or added to the tobacco material. Fermentation of the tobacco material can result in a modification of the flavor and aroma of the tobacco material. See, e.g., U.S. Pat. Nos. 4,528,993; 4,660, 577; 4,848,373 and 5,372,149, which are herein incorporated by reference in their entireties. In addition to modifying the aroma and/or flavor of the tobacco leaf, fermentation can change the color and/or texture of the fermented material. During the fermentation process, evolution gases can be produced, oxygen can be taken up, the pH can change, and the amount of water retained can change. See, e.g., U.S. Pub. No. 2005/0178398 and Tso (1999, Chapter 1 in Tobacco, Production, Chemistry and Technology, Davis & Nielsen, eds., Blackwell Publishing, Oxford), which are herein incorporated by reference in their entireties.

Conventionally, the moist oral snuff manufacturing process can be a lengthy process. Other conventional moist oral snuff products undergo an extensive aging and fermentation process. Conventionally, the length of time of the aging can be up to three years and the fermentation can vary from three weeks to eight weeks, for example. In certain conventional fermentation processes, various salt solutions and moisture are added to the tobacco material. A fermentation process is known to darken the color of the tobacco material, and can sometimes add what is referred to as a "barnyard" scent to the tobacco material. Under a conventional process for preparing such smokeless tobacco products, the tobacco material is typically fermented before adding any additional ingredients to the tobacco material for use in the final product and/or before packaging the final product. There are many different methods and recipes that have been used throughout the history of moist oral snuff products. Some conventional moist oral snuff products undergo very little or no fermentation.

For example, under a conventional manufacturing process, tobacco material, after harvest, can be packed for multiple years (e.g., 2 to 5 years) in hogsheads (i.e., large barrels) and aged under high moisture conditions (e.g., in the range of 18-22% moisture). It is noted that in some conventional moist snuff manufacturing processes, after harvest the tobacco plant can be hung in a barn for a period of time sufficient to at least partially dry the harvested tobacco plant prior to being placed in hogsheads. This process step is sometimes referred to by persons of ordinary skill in the art as "curing" the tobacco material. After enough time in the barrels (e.g., about 3 years) to allow for desirable biochemical changes to occur in the tobacco material, the tobacco material is removed from the hogsheads and moistened, at which time the tobacco material typically has a moisture content between 20-25%, or between about 20 and 22% moisture. The wet tobacco is then stored at room temperature (e.g., 15-25° C., or about 20-22° C.) in large batch tubs, such that it is exposed to an environment highly conducive to bacterial growth, promoting fermentation. It is noted that some people of ordinary skill in the art refer to this fermentation process as barrel fermentation". Throughout the present disclosure, conventional oral tobacco manufacturing processes are also referred to as batch and/or barrel and/or tub and/or tote fermentation processes, as they include this intermediary large batch fermentation process.

The resulting large batch fermentation in the barrels (also referred to as tubs or totes, for example) releases heat, raising the temperature of the mixture and promoting further bacterial growth and fermentation. During fermentation, the tobacco material must generally be moved/turned/agitated multiple times to interrupt bacterial growth, ensuring that the fermentation does not proceed uncontrolled (preventing the production of enough heat to kill bacteria). This fermentation process is typically allowed to continue for 60 to 90 days, and in some cases, until the manufacturer is satisfied that a desirable flavor level has been achieved. After fermentation in the big barrels, the tobacco material is chopped and dried and then casing materials (e.g., sugars, cocoa, salt, water, etc.) are added, raising the moisture level above about 40%-60%. The final mixture can then be packaged in smokeless tobacco cans or other packaging materials known in the art.

The above process (commonly referred to as a "large batch" fermentation process) associated with conventional moist oral snuff manufacturing processes requires time and expenses associated with monitoring the tubs, cleaning the tubs, rotating the tobacco materials as necessary, etc. in order to avoid issues such as "hot spots" that are associated with large scale fermentation processes (i.e., undesirable variations in temperature and moisture in various spots of the tobacco material throughout the large batch fermentation process). It has been surprisingly discovered, as disclosed herein, that tobacco materials useful in certain smokeless tobacco products, such as oral moist snuff, can be treated so as to allow for a fermentation process to be conducted in the final product packaging container, i.e., wherein the step of fermenting the tobacco material can occur after packaging the smokeless tobacco product. Such "in-can" fermentation can provide considerable cost benefits and enhanced efficiency in the overall processing of such smokeless tobacco products by eliminating the barrel fermentation step from conventional manufacturing processes.

The present disclosure provides such a process, as well as fermented tobacco material and smokeless tobacco products incorporating such fermented tobacco material. The fermented tobacco material of the present disclosure can be used as a component of a smokeless tobacco composition, such as loose moist snuff.

Figure 1A:
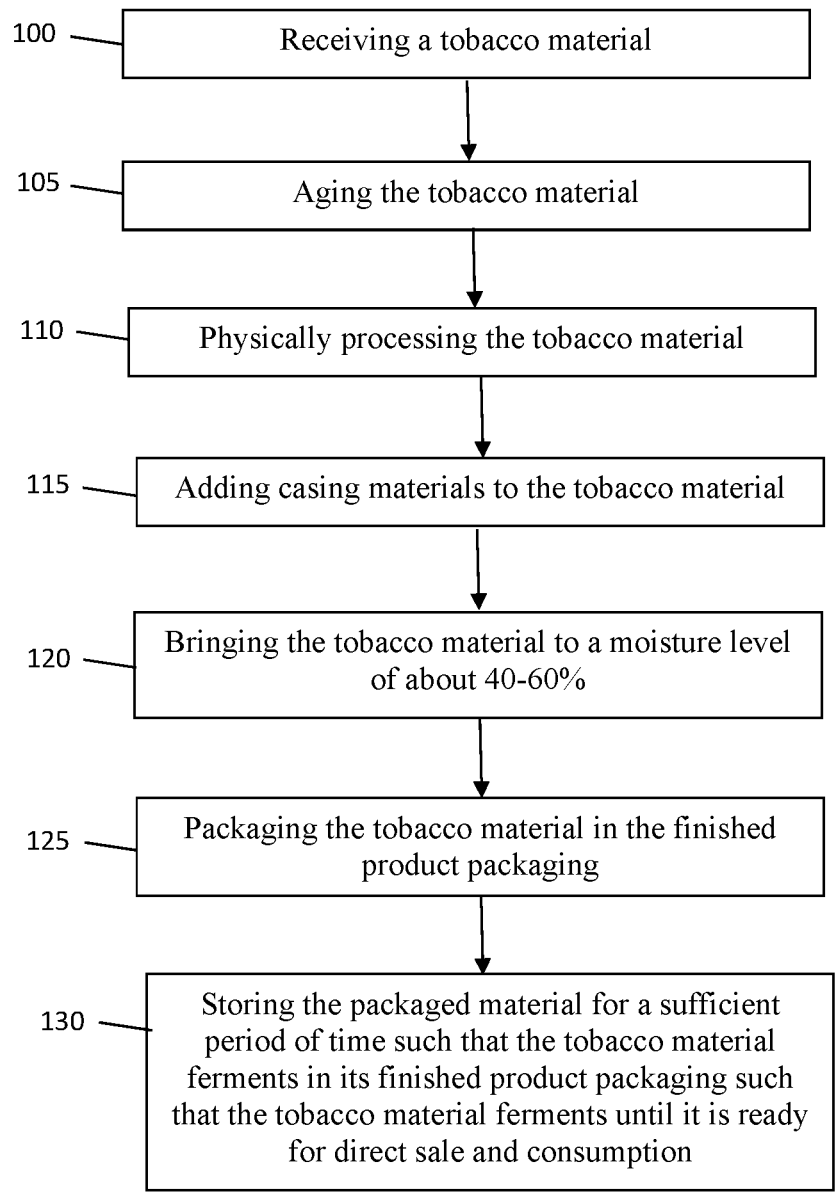
FIG. 1A is a flow chart illustrating the general steps for preparing a moist snuff tobacco product according to an embodiment of the present disclosure.

As illustrated at operation 100 of FIGS. 1 and 1A, for example, the manufacturing processes described herein include receiving a tobacco material. Tobaccos used in the tobacco material of the disclosure may vary. In certain embodiments, tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos and various blends of any of the foregoing tobaccos. Descriptions of various types of tobaccos, growing practices and harvesting practices are set forth in *Tobacco Production, Chemistry and Technology*, Davis et al. (Eds.) (1999), which is incorporated herein by reference. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia,* and *N. spegazzinii.*

*Nicotiana* species can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO 2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference. Most preferably, the tobacco materials are those that have been appropriately cured and aged. Especially preferred techniques and conditions for curing flue-cured tobacco are set forth in Nestor et al., Beitrage Tabakforsch. Int., 20 (2003) 467-475 and U.S. Pat. No. 6,895,974 to Peele, which are incorporated herein by reference. Representative techniques and conditions for air curing tobacco are set forth in Roton et al., Beitrage Tabakforsch. Int., 21 (2005) 305-320 and Staaf et al., Beitrage Tabakforsch. Int., 21 (2005) 321-330, which are incorporated herein by reference. Certain types of unusual or rare tobaccos can be sun cured. Manners and methods for improving the smoking quality of Oriental tobaccos are set forth in U.S. Pat. No. 7,025,066 to Lawson et al., which is incorporated herein by reference. Representative Oriental tobaccos include katerini, prelip, komotini, xanthi and yambol tobaccos. Tobacco compositions including dark air cured tobacco are set forth in US Patent Appl. Pub. No. 2008/0245377 to Marshall et al., which is incorporated herein by reference. See also, types of tobacco as set forth, for example, in US Patent Appl. Pub. No. 2011/0247640 to Beeson et al., which is incorporated herein by reference.

The *Nicotiana* species can be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be employed. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment.

The post-harvest processing of the plant or portion thereof can vary. Similar to some conventional moist snuff manufacturing processes, in the manufacturing processes described herein, after harvest the tobacco plant can be hung in a barn for a period of time sufficient to at least partially dry (i.e., cure) the harvested tobacco plant. As illustrated at operation 105 of FIG. 1A, for example, the manufacturing processes described herein can include aging the tobacco material. After harvest, the plant, or portion thereof, can be aged for a sufficient amount of time to develop the desired flavor and moisture characteristics of the tobacco material. In various embodiments, the tobacco material is aged in a barrel, e.g., a hogshead barrel, for a maximum of two to three years. The moisture level of the tobacco material after hogshead aging is typically in the range of 12-14%. It is noted that this step of aging the tobacco material can be conducted at any point in the process prior to final packaging (and fermentation). For example, in some embodiments, the tobacco material is allowed to age after step 110 (physically processing the tobacco material).

As illustrated at operation 110 of FIG. 1A, for example, the harvested plant or portion thereof can be physically processed. The plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment).

Although the tobacco material may comprise material from any part of a plant of the *Nicotiana* species, in certain embodiments, the majority of the material can comprise material obtained from the leaves, stems, stalks and/or roots of the plant. It is noted that typically, moist oral snuff comprises ground/pulverized tobacco leaves, however, the present disclosure is not limited thereto. For example, in certain embodiments, the tobacco material comprises at least about 90%, at least about 92%, at least about 95%, or at least about 97% by dry weight of the leaves of a harvested plant of the *Nicotiana* species. In certain embodiments, the starting tobacco material can include tobacco stems. As used herein, "stem" refers to the long thin part of a tobacco plant from which leaves or flowers grow, and can include the leaves, lamina, and/or flowers.

Tobacco compositions intended to be used in a smokeless form may incorporate a single type of tobacco (e.g., in a so-called "straight grade" form). For example, the tobacco within a tobacco composition may be composed solely of flue-cured tobacco (e.g., all of the tobacco may be composed, or derived from, either flue-cured tobacco lamina or a mixture of flue-cured tobacco lamina and flue-cured tobacco stem). In some embodiments, the tobacco within the tobacco composition can comprise dark fired tobacco and/or air-cured tobacco. The tobacco within a tobacco composition also may have a so-called "blended" form. For example, the tobacco within a tobacco composition of the present disclosure may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, in some embodiments, the tobacco material comprises 30-100% Dark Fired tobacco, 0-30% Green River tobacco, 0-70% One-Sucker tobacco, and up to 40% other tobacco materials (e.g., burley).

Portions of the tobaccos within the tobacco product may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. See, also, the types of tobacco processing techniques set forth in PCT WO 05/063060 to Atchley et al., which is incorporated herein by reference.

The tobacco material used in the present disclosure is typically provided in a shredded, ground, granulated, fine particulate, or powder form. The tobacco fermenting process described herein can include optionally milling a tobacco material. Most preferably, the tobacco is employed in the form of parts or pieces that have an average particle size less than that of the parts or pieces of shredded tobacco used in so-called "fine cut" tobacco products. Typically, the very finely divided tobacco particles or pieces are sized to pass through a screen of about 18 or 16 U.S. sieve size, generally are sized to pass a screen of about 20 U.S. sieve size, often are sized to pass through a screen of about 50 U.S. sieve size, frequently are sized to pass through a screen of about 60 U.S. sieve size, may even be sized to pass through a screen of 100 U.S. sieve size, and further may be sized so as to pass through a screen of 200 U.S. sieve size. It is noted that two scales commonly used to classify particle sizes are the U.S. Sieve Series and Tyler Equivalent. Sometimes these two scales are referred to as Tyler Mesh Size or Tyler Standard Sieve Series. U.S. sieve size is referred to in the present application. If desired, air classification equipment may be used to ensure that small sized tobacco particles of the desired sizes, or range of sizes, may be collected. In one embodiment, the tobacco material is in particulate size sized to pass through an 18 or 16 U.S. sieve size, but not through a 60 U.S. sieve size. If desired, differently sized pieces of granulated tobacco may be mixed together. Oral moist snuff products can be characterized as coarse-grained, medium-grained, and fine-grained. Typically, the tobacco particles or pieces suitable for moist oral snuff products according to the present disclosure have a particle size less than U.S. sieve size 50, often 14 to 45 U.S. sieve size, frequently 14 to 30 U.S. sieve size. In various embodiments, oral moist snuff products according to the present disclosure are coarse-grained. In certain embodiments, the tobacco is provided with an average particle size of about 0.2 to about 2 mm, about 0.5 to about 1.5 mm, about 0.2 to about 1.0 mm, or about 0.75 to about 1.25 mm (e.g., about 1 mm).

In various embodiments, the tobacco material can be treated to extract one or more soluble components of the tobacco material therefrom. Methods for extracting are generally known; see, for example, the extraction processes described in US Pat. Appl. Pub. No. 2011/0247640 to Beeson et al.; and U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein. In some embodiments, the extract could be added to a tobacco material to be fermented according to the present disclosure. In various embodiments, at least a portion of the tobacco material subjected to the fermentation processes described herein can comprise the residual pulp from an extraction process.

Tobacco materials described herein can be whitened in certain embodiments according to any means known in the art, e.g., prior to being subjected to a fermentation as disclosed herein. For example, whitening methods using various bleaching or oxidizing agents and oxidation catalysts can be used. See, e.g., the processes disclosed in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; and U.S. Pat. No. 5,713,376 to Berger; and PCT WO 96/31255 to Giolvas; and U.S. patent application Ser. No. 16/227,742 filed Dec. 20, 2018; all of which are incorporated herein by reference.

The tobacco materials discussed in the present disclosure can be treated and/or processed in other ways before, after, or during the process steps described herein. For example, if desired, the tobacco materials can be irradiated, pasteurized, or otherwise subjected to controlled heat treatment. Such treatment processes are detailed, for example, in US Pat. Pub. No. 2009/0025738 to Mua et al., which is incorporated herein by reference. In certain embodiments, the tobacco materials can undergo a pulping process. See, e.g., U.S. Patent Appl. Pub. No. 2013/0276801 to Byrd Jr. et al., herein incorporated by reference in its entirety.

As discussed above, conventionally, tobacco materials for use in certain smokeless tobacco products which are subjected to a fermentation process undergo an intermediary large batch barrel fermentation process before the final smokeless tobacco product is packaged and sometimes before additional ingredients (e.g., casing materials) are added to the tobacco material. In the processes described herein, the tobacco materials are not intentionally subjected to any substantial fermentation process prior to packaging the individual final smokeless tobacco products. Rather, the (unfermented) tobacco material to be subjected to fermentation is directly packaged in a manner so as to ensure that the conditions within the package are suitable to promote fermentation. Accordingly, fermentation of the tobacco material occurs within the final product packaging container, as described in more detail below. Furthermore, any additional ingredients to be included in the final tobacco composition (e.g., top dressing components such as water, salt, carbonates, and flavorings) are added prior to (or at the same time as) packaging and, thus, prior to the subsequent "in-can" fermentation process.

In certain embodiments, microorganisms can be added to the tobacco material before it is added to the product containers to promote the "in-can" fermentation, although it is noted that, in some embodiments, fermentation may proceed within the individual containers in the absence of added microorganisms (e.g., as microorganisms may be associated with the tobacco material itself and may serve to promote the fermentation). For example, microorganisms that can be added to the tobacco material include, but are not limited to *Tetragenococcus, Staphylococcus nepalensis, Lactobacillus, Weissella, Leuconostoc*, and combinations thereof. Microorganisms that are useful in the manufacturing processes described herein include microorganisms that cannot convert nitrate to nitrite and that can handle the high pH, high salt content, and low water activity conditions within the containers. In certain embodiments, *Tetragenococcus* microorganisms are particularly useful to promote fermentation in containers according to the present disclosure. *Staphylococcus nepalensis* can convert nitrate to nitrite, but it works at high pH and at high salt content so the nitrite, if formed, might be converted to a compound that keeps nitrite low. It is noted that the high salt content found in certain casing materials could affect the enzyme that converts the nitrate to nitrite. In various embodiments, about 100-1,000,000 bacteria/g of tobacco can be added to the tobacco material.

The relative amount of tobacco material within the smokeless tobacco composition may vary. Preferably, the amount of tobacco material within the smokeless tobacco composition is at least about 50%, at least about 60%, at least about 70%, at least about 80%, or at least about 90% on a dry weight basis of the formulation. A typical range of tobacco material within the formulation is about 50 to about 99%, more often about 80 to about 99% by weight on a dry basis.

As illustrated in FIG. 1A, for example, at operation 115 casing materials can be added to the tobacco material prior to packaging. Casing materials such as licorice, flavorants, and sugars are applied to the tobacco material. Casing materials known in the art can affect the delivery of nicotine and thereby produce "milder" tobacco products. Those having skill in the art will be able to formulate specific blends of casing materials useful in the smokeless tobacco products disclosed herein. The step of casing is normally carried out at a temperature over 140° F. (60° C.), preferably in the range of about 140°-190° F. (60°-88° C.), and more preferably at about 190° F. (88° C.). See, e.g., U.S. Pat. No. 4,528,993, which is incorporated herein by reference. In various embodiments of the manufacturing processes described herein, casing can place the tobacco material into a forced aging stage which simulates a microbial fermentation process which can be a natural fermentation (i.e., because tobacco materials already include microorganisms), or can be supplemented by microorganisms and/or other casing materials added to the tobacco materials.

Depending on the type of tobacco product being processed, the tobacco product can include one or more additional components in addition to the tobacco material as described above. For example, the tobacco material can be processed, blended, formulated, combined and/or mixed with other materials or ingredients, such as other tobacco materials or flavorants, fillers, binders, pH adjusters, buffering agents, salts, sweeteners, colorants, oral care additives, disintegration aids, antioxidants, humectants, and preservatives. See, for example, those representative components, combination of components, relative amounts of those components and ingredients relative to tobacco, and manners and methods for employing those components, set forth in US Pat. Pub. Nos. 2011/0315154 to Mua et al.; 2007/0062549 to Holton, Jr. et al.; 2012/0067361 to Bjorkholm et al.; 2017/0020183 to Bjorkholm; and 2017/0112183 to Bjorkholm; and U.S. Pat. No. 7,861,728 to Holton, Jr. et al., each of which is incorporated herein by reference.

In some embodiments, the container includes all of the components intended to be contained within the final product. For example, in various embodiments, the moist oral snuff products described herein comprise a tobacco material, salt (e.g., NaCl), and water. See, e.g., U.S. Pat. Pub. No. 2017/0280764, which is incorporated herein by reference in its entirety. Types of salts useful in the moist oral snuff compositions described herein include, but are not limited to, sodium chloride, potassium chloride, sodium citrate, potassium citrate, sodium acetate, potassium acetate, and the like.

Example flavorants that can be used are components, or suitable combinations of those components, that act to alter the bitterness, sweetness, sourness, or saltiness of the smokeless tobacco product, enhance the perceived dryness or moistness of the formulation, or the degree of tobacco taste exhibited by the formulation. Flavorants may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/cocoa, cream, mint, spearmint, menthol, peppermint, wintergreen, eucalyptus, lavender, cardamon, nutmeg, cinnamon, clove, cascarilla, sandalwood, honey, jasmine, ginger, anise, sage, licorice, lemon, orange, apple, peach, lime, cherry, strawberry, and any combinations thereof. See also, Leffingwell et al., Tobacco Flavoring for Smoking Products, R. J. Reynolds Tobacco Company (1972), which is incorporated herein by reference. Flavorings also may include components that are considered moistening, cooling or smoothening agents, such as eucalyptus. These flavors may be provided neat (i.e., alone) or in a composite (e.g., spearmint and menthol, or orange and cinnamon). Example flavorant compositions include various top dressing and casing compositions, including those compositions described in U.S. Pat. No. 5,121,757 to White et al.; U.S. Pat. No. 5,370,139 to Shu et al.; U.S. Pat. No. 5,318,050 to Gonzalez-Parra et al.; U.S. Pat. No. 5,343,879 to Teague; U.S. Pat. No. 5,413,122 to Shu et al.; U.S. Pat. No. 5,387,416 to White et al.; U.S. Pat. No. 5,962,662 to Shu et al.; U.S. Pat. No. 6,048,404 to White; U.S. Pat. No. 6,298,858 to Coleman, III, et al.; U.S. Pat. No. 6,325,860 to Coleman, III; U.S. Pat. No. 6,428,624 to Coleman, III, et al.; U.S. Pat. No. 6,591,841 to White et al.; and U.S. Pat. No. 6,695,924 to Dube et al.; and US Pat. App. Pub. Nos. 2004/0173228 to Coleman, III; 2005/0244521 to Strickland et al.; and PCT Application Pub. No. WO 05/041699 to Quinter et al.; all of which are incorporated by reference herein. The amount of flavorants utilized in the tobacco composition can vary, but is typically up to about 10 dry weight percent, and certain embodiments are characterized by a flavorant content of at least about 1 dry weight percent, such as about 1 to about 10 dry weight percent. Combinations of flavorants are often used.

Flavorants in the form of sweeteners can also be added to the moist oral snuff compositions described herein. Sweeteners can include natural sweeteners (e.g., fructose, sucrose, glucose, maltose, mannose, galactose, lactose, and the like), artificial sweeteners (e.g., sucralose, saccharin, aspartame, acesulfame K, neotame, and the like); and mixtures thereof.

Preferred pH adjusters or buffering agents provide and/or buffer within a pH range of about 6 to about 10, and example agents include metal hydroxides, metal carbonates, metal bicarbonates, and mixtures thereof. Specific example materials include citric acid, sodium hydroxide, potassium hydroxide, potassium carbonate, sodium carbonate, and sodium bicarbonate. The amount of pH adjuster or buffering material utilized in the tobacco composition can vary, but is typically up to about 5 dry weight percent, and certain embodiments can be characterized by a pH adjuster/buffer content of less than about 0.5 dry weight percent, such as about 0.05 to about 0.2 dry weight percent.

Example humectants include glycerin and propylene glycol. The amount of humectant utilized in the tobacco composition can vary, but is typically up to about 5 dry weight percent, and certain embodiments can be characterized by a humectant content of at least about 1 dry weight percent, such as about 2 to about 5 dry weight percent.

Other ingredients such as preservatives (e.g., potassium sorbate), and/or antioxidants can also be used. Typically, such ingredients, where used, are used in amounts of up to about 10 dry weight percent and usually at least about 0.1 dry weight percent, such as about 0.5 to about 10 dry weight percent. A disintegration aid is generally employed in an amount sufficient to provide control of desired physical attributes of the tobacco formulation such as, for example, by providing loss of physical integrity and dispersion of the various component materials upon contact of the formulation with water (e.g., by undergoing swelling upon contact with water).

In some embodiments, any of the components described above can be added in an encapsulated form (e.g., in the form of microcapsules), the encapsulated form comprising a wall or barrier structure defining an inner region and isolating the inner region permanently or temporarily from the tobacco composition. The inner region includes a payload of an additive either adapted for enhancing one or more sensory characteristics of the smokeless tobacco product, such as taste, mouthfeel, moistness, coolness/heat, and/or fragrance, or adapted for adding an additional functional quality to the smokeless tobacco product, such as addition of an antioxidant or immune system enhancing function. See, for example, the subject matter of US Pat. Appl. Pub. No. 2009/0025738 to Mua et al., which is incorporated herein by reference.

The components of the tobacco composition can be brought together in admixture using any mixing technique or equipment known in the art. The optional components noted above, which may be in liquid or dry solid form, can be admixed with the tobacco material in a pretreatment step prior to mixture with any remaining components of the composition or simply mixed with the tobacco material together with all other liquid or dry ingredients prior to introducing the material to the final container. Any mixing method that brings the tobacco composition ingredients into intimate contact can be used. A mixing apparatus featuring an impeller or other structure capable of agitation is typically used.

Example mixing equipment includes casing drums, conditioning cylinders or drums, liquid spray apparatus, conical-type blenders, ribbon blenders, mixers available as FKM130™, FKM600™, FKM1200™, FKM2000™ and FKM3000™ from Littleford Day, Inc., Plough Share types of mixer cylinders, and the like.

As such, the overall mixture of various components with the tobacco material may be relatively uniform in nature. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. Manners and methods for formulating snus-type tobacco formulations will be apparent to those skilled in the art of snus tobacco product production. It is noted that additional components of the moist oral snuff compositions described herein can, in some embodiments, be introduced independently from the tobacco material into final product packaging.

The moisture content of the smokeless tobacco product prior to packaging may vary. For conventional moist oral snuff products, the moisture content of the product before packaging (after being fermented and dried), is less than about 55 weight percent, generally is less than about 50 weight percent, and often is less than about 45 weight percent. For certain tobacco products prepared according to the present disclosure, such as those incorporating snus-types of tobacco compositions, the moisture content of the tobacco material before packaging may exceed 45 weight percent, and often may exceed 50 weight percent. For example, a representative snus-type product may possess a tobacco composition exhibiting a moisture content of about 45 weight percent to about 60 weight percent, preferably about 50 weight percent to about 55 weight percent.

As illustrated at operation 120 in FIGS. 1 and 1A, for example, the tobacco material (mixed with the optional additional ingredients) can be brought to a desired moisture level before packaging. The manner by which the moisture content of the formulation is controlled may vary. For example, the formulation may be subjected to thermal or convection heating. As a specific example, the formulation may be oven-dried, in warmed air at temperatures of about 40° C. to about 95° C., with a preferred temperature range of about 60° C. to about 80° C. for a length of time appropriate to attain the desired moisture content. Alternatively, tobacco formulations may be moistened using casing drums, conditioning cylinders or drums, liquid spray apparatus, ribbon blenders, or mixers.

The acidity or alkalinity of the tobacco formulation, which is often characterized in terms of pH, can vary. Typically, the pH of that formulation is at least about 6.5, and preferably at least about 7.5. In some embodiments, the pH of that formulation will not exceed about 11, or will not exceed about 9, and often will not exceed about 8.5. A representative tobacco formulation exhibits a pH of about 6.8 to about 8.2 (e.g., about 7.8). A representative technique for determining the pH of a tobacco formulation involves dispersing 5 g of that formulation in 100 ml of high performance liquid chromatography water, and measuring the pH of the resulting suspension/solution (e.g., with a pH meter).

As illustrated at operation 125 in FIGS. 1 and 1A, in various embodiments moist oral snuff manufacturing process can include packaging the tobacco material. The smokeless tobacco product can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; D592,956 to Thiellier; D594,154 to Patel et al.; and D625, 178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; 2011/0168712 to Bailey et al.; and 2011/0204074 to Gelardi et al., which are incorporated herein by reference. Products of the present disclosure may be packaged, sealed, and stored in much the same manner that conventional types of smokeless tobacco products are packaged and stored. For example, the packaged tobacco material can be stored at ambient temperatures for at least about 20-30 days. In certain embodiments, the packaged tobacco material is stored at a temperature not greater than about 105° F.

It is noted that as used herein, "sealing a final product" can include sealing or at least partially sealing the container with a label or wrapper of a pervious or impervious material, wherein the label is configured to substantially cover at least a portion of the outer surface of the container. See, e.g., the containers and labels described in U.S. Pat. Pub. No. 2019/0261681 to Playford et al., which is herein incorporated by reference. "Sealing a final product container" can also refer to securely closing the product container. For example, the container may comprise a lid and a base, and the container can include a means for securing or sealing the lid to the base of the container. See, e.g., U.S. Pat. Pub. No. 2014/0197054 to Pipes et al., which is herein incorporated by reference. The means for securing the lid to the base may include a vent structure, which can allow for gases to enter and/or leave the "sealed" container. See, e.g., the containers and labels described in U.S. Pat. Pub. No. 2019/0261681 to Playford et al. and in U.S. Pat. Pub. No. 2014/0197054 to Pipes et al, which are incorporated by reference in their entireties.

In various embodiments, the tobacco composition according to the present disclosure may be contained in a container used to contain smokeless tobacco products, such as a cylindrical container sometimes referred to as a "puck". These containers into which the tobacco composition is added, in some embodiments, are the final consumer product packaging, and are typically of conventional size for such final consumer product packaging. The container can be any shape, and is not limited to cylindrical containers. Such containers may be manufactured out of any suitable material, such as metal, molded plastic, fiberboard, combinations thereof, etc. If desired, moist tobacco products (e.g., products having moisture contents of more than about 20 weight percent) may be refrigerated (e.g., at a temperature of less than about 10° C., often less than about 8° C., and sometimes less than about 5° C.). Alternatively, relatively dry tobacco products (e.g., products having moisture contents of less than about 15 weight percent) often may be stored under a relatively wide range of temperatures.

As described above, smokeless tobacco products of the present disclosure do not comprise tobacco that has been intentionally fermented prior to incorporation within a final product container; rather, they undergo a fermentation process after being packaged in the final product container. General process steps for fermenting a tobacco material according to the present disclosure are illustrated in FIGS. 1 and 1A.

In some embodiments, the temperature at which the packaged moist oral snuff products are stored during the in-can fermentation is increased to a first elevated temperature, to cause sporulation of at least a portion of any dormant spore forming bacteria (i.e. *Bacillus* sp.) associated with the tobacco material. This first elevated temperature can vary, but is generally at least about 80° F. or at least about 85° F., such as within the range of about 85° F. to about 105° F. This first elevated temperature is maintained for a sufficient time period to allow sporulation to occur (e.g., at least about 5 minutes, at least about 10 minutes, at least about 15 minutes, or at least about 30 minutes, such as between about 5 and about 60 minutes).

In some embodiments, the temperature is then further increased to a second elevated temperature, to heat kill vegetative bacteria. This second elevated temperature can vary, but is generally at least about 150° F. or at least about 160° F., such as within the range of about 160° F. to about 212° F. This temperature is maintained for a sufficient time period to provide a reduction in the number of living vegetative bacteria (e.g., at least about 5 minutes, at least about 10 minutes, at least about 15 minutes, or at least about 30 minutes). However, in certain embodiments, this time period is advantageously controlled so as to ensure that no substantial tobacco-specific nitrosamine formation occurs. For example, this time period can, in some embodiments, be between about 5 and about 60 minutes. The packaged products (e.g., moist oral snuff packaged in a puck) are subsequently cooled, e.g., to about 100° F. or less, such as between about 85° F. and about 100° F. In certain embodiments of the manufacturing processes described herein, the temperature of the fermenting tobacco is advantageously controlled (e.g., maintained) throughout the fermentation process. Example temperatures at which the tobacco material is maintained are within the range of about 80° F. to about 95° F. Methods for controlling the temperature are generally known. In some embodiments, the temperature of the pucks after packaging is not increased and the pucks are simply stored at about ambient temperature, or at a temperature of no greater than about 105° F. for the entire in-can fermentation process. As illustrated at operation 130 of FIG. 1, for example, the packaged tobacco material can be stored at a temperature of at least about 80° F. for at least about 2 weeks to give the desired fermented product.

The time for which the tobacco material is maintained under these conditions can vary. Typically, the tobacco material is maintained under these conditions until a desirable level of fermentation is achieved. In some embodiments, fermentation can be monitored by evaluating the level of, e.g., malic and citric acid, which are depleted during fermentation. Although not intended to be limiting, example fermentation times can be at least about 2 weeks or at least about 3 weeks, e.g., about 3 to about 4 weeks. These values can vary, e.g., depending on such parameters as inoculation rate, moisture, temperature, pH, salinity, and aeration. The final pH of the tobacco material following a successful fermentation should be approximately 7.6-7.9. Furthermore, the levels of nitrite and TSNA should be as low as possible. In some embodiments, the nitrite is less than about 10 ppm, or less than about 8 ppm in the tobacco material after the in-can fermentation is complete. In some embodiments, the TSNA is less than about 10 ppm, or less than about 8 ppm in the tobacco material after the in-can fermentation is complete.

As illustrated in Example 1 below, the same, or at least similar, level of organic acids are present in the moist oral snuff products prepared using an in-can fermentation as compared to conventional moist oral snuff products wherein an intermediary barrel fermentation process occurs before packaging. Accordingly, despite using a different manufacturing process, a comparable extent of fermentation can occur (as evaluated, e.g., by organic acid content) in products undergoing an in-can fermentation as products undergoing conventional pre-packaging fermentation. Furthermore, the disclosed fermentation method advantageously and surprisingly eliminates a step associated with conventional production methods of moist snuff products (i.e., large batch fermentation) while providing a comparable end product.

The following examples are provided to further illustrate embodiments of the present disclosure, but should not be construed as limiting the scope thereof. Unless otherwise noted, all parts and percentages are by weight.

EXPERIMENTAL

Embodiments of the present disclosure are more fully illustrated by the following examples, which are set forth to illustrate aspects of the present disclosure and are not to be construed as limiting thereof. In the following examples, g means gram, L means liter, mL means milliliter, and Da means daltons. All weight percentages are expressed on a dry basis, meaning excluding water content, unless otherwise indicated.

Example 1

A moist snuff smokeless tobacco composition was prepared according to the present disclosure (referenced below as an "all-in" sample). A moist snuff smokeless tobacco composition according to traditional fermentation methods was also prepared and packaged for comparison purposes (i.e., a process including a step of large batch fermentation in a tote/tub prior to packaging). The samples prepared according to traditional fermentation methods are referenced below as "tub" samples. The final product ingredients (e.g., casing materials) used and the amounts thereof in each of the samples were the substantially the same. The tobacco material used in each of the samples was an aged tobacco material.

The "all-in" samples according to the present disclosure are prepared using lab-scale equipment. All ingredients are added to a blender, the mixture is agitated to achieve a uniformly mixed product, and the completed blend is discharged into tubs to await packaging in finished product cans. Water is added to the tobacco composition such that the tobacco composition has a moisture content of about 51-55%. The final product composition is then packaged in individual puck containers and allowed to ferment in the individual pucks.

The "tub" samples according to conventional fermentation processes are prepared by first adding water to tobacco stems and leaves and fermenting the tobacco materials in large batch tubs according to conventional fermentation methods known in the art. The fermented tobacco materials were then cut and dried. The tobacco input was then admixed with all other components of the final product composition. Water was added to the tobacco composition such that the tobacco composition has a moisture content of about 51-55%. The final product composition was then packaged in individual puck containers.

Figure 2A:
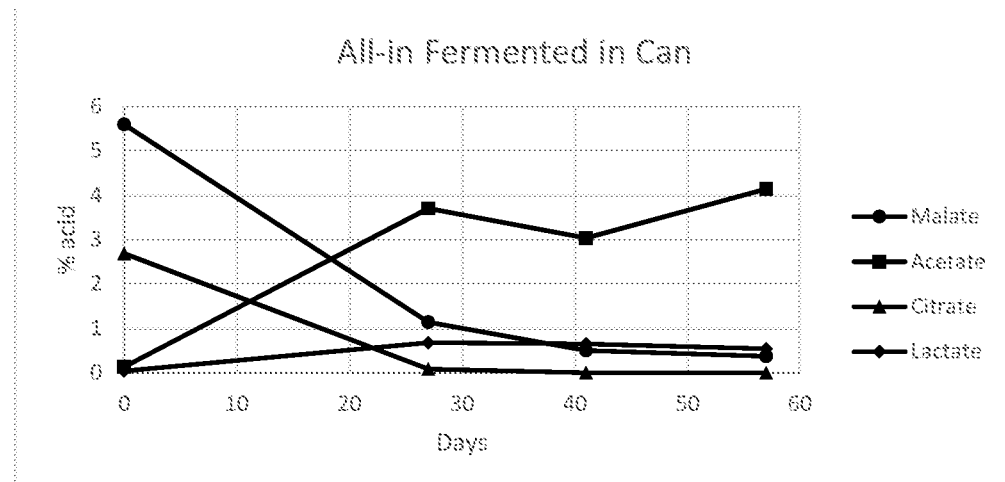
FIG. 2A is a graph showing the levels of various acids in samples prepared according to the present disclosure over time.
Figure 2B:
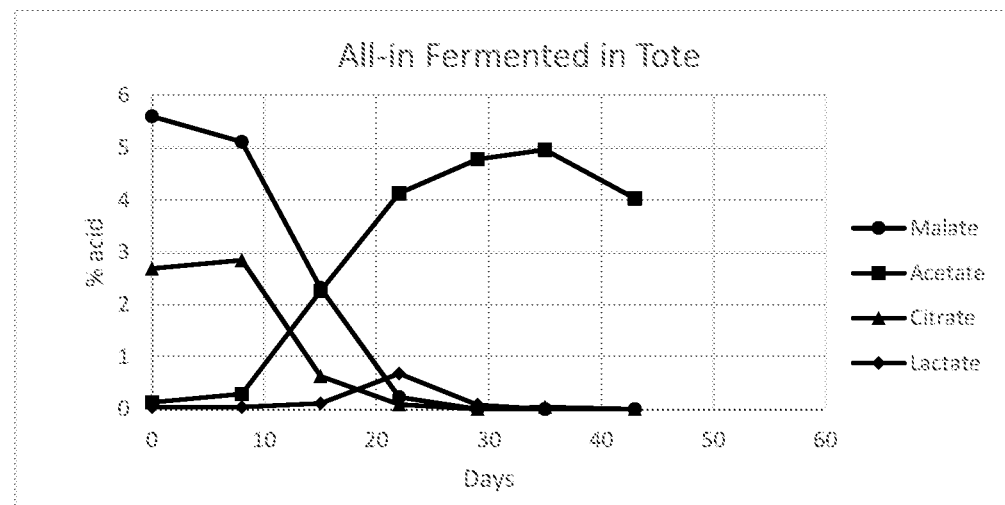
FIG. 2B is a graph showing the levels of various acids in samples prepared according to conventional fermentation methods (i.e., including a fermentation process in a tote/tub) over time.

The amount of malic acid, acetic acid, lactic acid, and citric acid was measured using Gas Chromatography with Flame Ionization Detection for each of the samples according to the present disclosure and for the samples prepared according to conventional fermentation methods. A malate drop, an acetate increase, and a slight drop in citrate are indicative of a composition with good stability. FIG. 2A shows the amount of each acid present in the samples prepared according to the present disclosure (i.e., fermenting in the puck) over about 60 days. FIG. 2B shows the amount of each acid present in the samples prepared according to conventional fermentation methods over about 45 days. As can be seen from FIGS. 2A and 2B, the levels of the measured acids in the two manufacturing processes is comparable. It was surprisingly discovered in the present application that the intermediary fermentation process associated with conventional oral moist snuff manufacturing processes can be eliminated, and still provide a comparable fermented material, e.g., as evidenced by similar acid content.

Figure 3A:
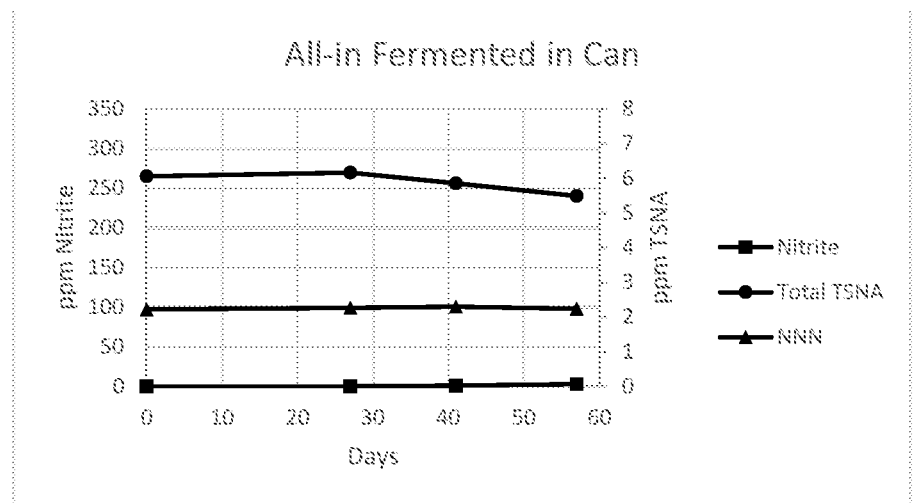
FIG. 3A is a graph showing the levels of TSNAs (including, specifically, NNN), and nitrite in samples prepared according to the present disclosure over time.
Figure 3B:
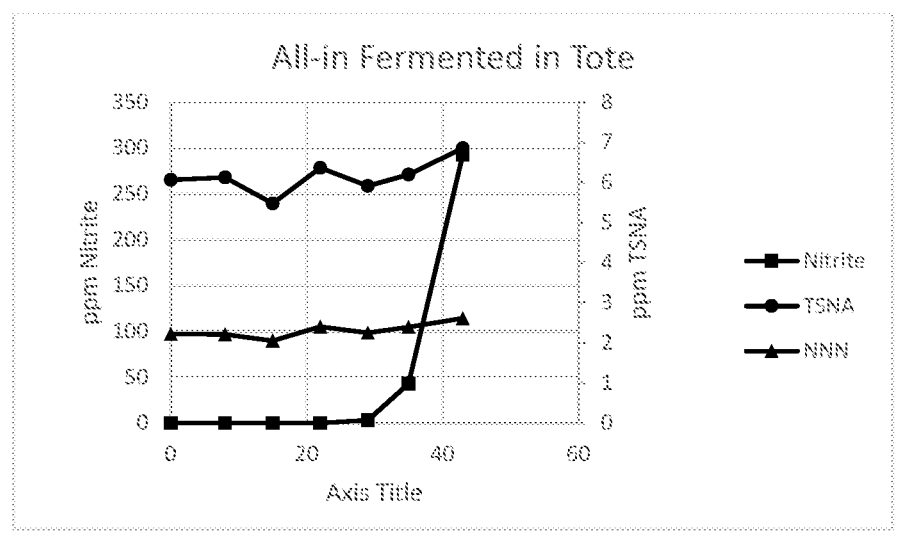
FIG. 3B is a graph showing the levels of TSNAs (including, specifically, NNN), and nitrite in samples prepared according to conventional fermentation methods (i.e., including a fermentation process in a tote/tub) over time.

The levels of TSNA and nitrite was measured (in ppm) for each of the samples according to the present disclosure and for the samples prepared according to conventional fermentation methods. HPLC-LC/MS was used to gather the measurements. No increase in nitrite or TSNA is preferred. FIG. 3A shows the levels of TSNA and nitrite present in the samples prepared according to the present disclosure (i.e., fermenting in the puck) over about 60 days. FIG. 3B shows the TSNA and nitrite present in the samples prepared according to conventional fermentation methods over about 45 days.

Many modifications and other embodiments will come to mind to one skilled in the art to which this disclosure pertains having the benefit of the teachings presented in the foregoing description. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method of preparing a smokeless tobacco product, comprising:
   (i) receiving a tobacco material;
   (ii) adding water to the tobacco material to form a tobacco composition having a moisture content of at least about 40%;
   (iii) packaging the tobacco composition in an individual storage container, wherein the individual storage container is a final salable consumer distribution container configured for retail distribution, wherein the individual storage container allows for gases to enter and/or leave the individual storage container;
   (iv) putting the individual storage container into a sleeve with additional individual storage containers;
   (v) putting the sleeve, alone or in combination with one or more additional sleeves into boxes;
   (vi) placing the boxes onto pallets; and
   (vii) allowing the tobacco composition to ferment in the individual storage container for at least 25 days,
   wherein the process further comprises adding at least one microorganism selected from the group consisting of *Tetragenococcus, Staphylococcus nepalensis, Lactobacillus, Weissella, Leuconostoc*, and combinations thereof to the tobacco composition prior to step (iii), or wherein no microorganisms are added to the tobacco composition, and
   wherein the tobacco material is not intentionally subjected to any substantial fermentation process prior to step (iii).

2. The method according to claim 1, wherein the smokeless tobacco product is moist oral snuff.

3. The method according to claim 1, wherein the moisture content of the tobacco composition is about 51-53% prior to the step of packaging the tobacco composition.

4. The method according to claim 1, further comprising adding casing materials to the tobacco material prior to packaging the tobacco composition.

5. The method according to claim 4, wherein the casing materials comprise at least one of a salt, a flavorant, a sugar, and a carbonate.

6. The method according to claim 4, wherein the casing materials comprise a flavorant selected from the group consisting of licorice flavorant, cocoa flavorant, and combinations thereof.

7. The method according to claim 1, further comprising adding at least one additive to the tobacco material prior to packaging the tobacco composition.

8. The method according to claim 7, wherein the additive is selected from the group consisting of water, flavorants, binders, colorants, pH adjusters, buffering agents, fillers, disintegration aids, humectants, antioxidants, oral care ingredients, preservatives, additives derived from herbal or botanical sources, and mixtures thereof.

9. The method according to claim 8, wherein the additive comprises at least one salt.

10. The method of claim 1, wherein the process comprises adding the at least one microorganism selected from the group consisting of *Tetragenococcus, Staphylococcus nepalensis, Lactobacillus, Weissella, Leuconostoc*, and combinations thereof to the tobacco composition prior to step (iii).

11. The method of claim 1, wherein no microorganisms are added to the tobacco composition.

12. The method of claim 1, wherein step (vii) is conducted at room temperature.

13. The method of claim 1, wherein the tobacco material is aged.

14. The method of claim 1, wherein the step (iii) of packaging the tobacco material includes sealing or at least partially sealing the individual storage container with a label or wrapper of a pervious or impervious material, wherein the label is configured to substantially cover at least a portion of the outer surface of the individual storage container.

15. The method of claim 1, wherein the individual storage container comprises a lid and a base and the container includes a means for securing or sealing the lid to the base of the container, comprising a vent structure which allows for gases to enter and/or leave the individual storage container.

16. The method of claim 1, wherein the individual storage container is a can or puck.

* * * * *